US012778758B2

(12) United States Patent
Chon et al.

(10) Patent No.: US 12,778,758 B2
(45) Date of Patent: Nov. 3, 2026

(54) METHOD FOR DESIGNING OF IMPLANT USE FOR THE FINGER BONES

(71) Applicant: JEIL MEDICAL CORPORATION, Seoul (KR)

(72) Inventors: Chang-Soo Chon, Gimpo-si (KR); Hyo-Chul Shin, Seoul (KR); Dae-Dong Kim, Hanam-si (KR)

(73) Assignee: JEIL MEDICAL CORPORATION, Seoul (KR)

( * ) Notice: Subject to any disclaimer, the term of this patent is extended or adjusted under 35 U.S.C. 154(b) by 993 days.

(21) Appl. No.: 18/010,509

(22) PCT Filed: Jun. 10, 2022

(86) PCT No.: PCT/KR2022/008250
§ 371 (c)(1),
(2) Date: Dec. 15, 2022

(87) PCT Pub. No.: WO2023/075064
PCT Pub. Date: May 4, 2023

(65) Prior Publication Data
US 2023/0338157 A1 Oct. 26, 2023

(30) Foreign Application Priority Data
Oct. 26, 2021 (KR) ........................ 10-2021-0143325

(51) Int. Cl.
*A61F 2/30* (2006.01)
*A61B 34/10* (2016.01)
(Continued)

(52) U.S. Cl.
CPC .......... *A61F 2/30942* (2013.01); *A61B 34/10* (2016.02); *A61F 2/4241* (2013.01);
(Continued)

(58) Field of Classification Search
CPC ................ A61F 2/30942; A61F 2/4241; A61F 2002/30943; A61F 2002/30948;
(Continued)

(56) References Cited

U.S. PATENT DOCUMENTS 8,775,133 B2 * 7/2014 Schroeder ................ A61F 2/30 703/1
11,229,519 B2 * 1/2022 Radermacher ......... A61B 17/15
(Continued)

FOREIGN PATENT DOCUMENTS

CN 104546237 A 4/2015
CN 107174381 A 9/2017
(Continued)

OTHER PUBLICATIONS

Gibson, I. et al. "Chapter 9: The Development of an Artificial Finger Joint" Bio-Materials & Prototyping Applications in Medicine, pp. 157-190 (2008) available from <https://link.springer.com/chapter/10.1007/978-0-387-47683-4_9> (Year: 2008).*
(Continued)

*Primary Examiner* — Jay Hann
(74) *Attorney, Agent, or Firm* — NKL Law; Jae Youn Kim

(57) ABSTRACT

A method for designing an implant for finger bones, the method including a finger bone image collection step of collecting 3D images of several human finger bones, a finger bone measurement step of measuring the length, cross-sectional width, and thickness of each of the finger bones from the 3D images of the finger bones, and an implant shape derivation step of calculating average values of the lengths, cross-sectional widths, and thicknesses of the finger bones and deriving and storing the shapes of implants for
(Continued)

finger bones into a database on the basis of the calculated average values of the cross-sectional widths and thicknesses and shapes of cut surfaces.

6 Claims, 11 Drawing Sheets

(51) Int. Cl.
*A61F 2/42* (2006.01)
*G06T 7/62* (2017.01)

(52) U.S. Cl.
CPC .......... *G06T 7/62* (2017.01); *A61B 2034/108* (2016.02); *A61F 2002/30943* (2013.01); *A61F 2002/30948* (2013.01); *A61F 2002/30985* (2013.01); *G06T 2200/04* (2013.01); *G06T 2207/10081* (2013.01); *G06T 2207/10088* (2013.01); *G06T 2207/10116* (2013.01); *G06T 2207/30008* (2013.01)

(58) Field of Classification Search
CPC .............. A61F 2002/30985; A61F 2/28; A61F 2002/4633; A61F 2002/30952; A61F 2002/3096; A61B 34/10; A61B 2034/108; A61B 2034/105; G06T 7/62; G06T 2200/04; G06T 2207/10081; G06T 2207/10088; G06T 2207/10116; G06T 2207/30008; G06T 2207/10028; B33Y 50/00
See application file for complete search history.

(56) References Cited

U.S. PATENT DOCUMENTS

| | | | | |
|---|---|---|---|---|
| 2010/0217270 | A1* | 8/2010 | Polinski | A61F 2/30942 700/98 |
| 2014/0228860 | A1* | 8/2014 | Steines | A61B 34/10 606/130 |
| 2020/0163703 | A1* | 5/2020 | Sperling | A61B 17/8061 |

FOREIGN PATENT DOCUMENTS

| | | | |
|---|---|---|---|
| JP | 2006-501977 | A | 1/2006 |
| JP | 2015-516199 | A | 6/2015 |
| KR | 10-1994-7001237 | A | 5/1994 |
| KR | 10-2011-0139229 | A | 12/2011 |
| KR | 10-2017-0018023 | A | 2/2017 |

OTHER PUBLICATIONS

Novel implant design of the proximal interphalangeal joint using an optimized rolling contact joint mechanism, Seok Woo Hong et al., Journal of Orthopaedic Surgery and Research, 2019, vol. 14, Article No. 212, pp. 1-13.

* cited by examiner

METHOD FOR DESIGNING OF IMPLANT USE FOR THE FINGER BONES

TECHNICAL FIELD

The present disclosure relates to a method for designing an implant for a finger bone. In more detail, the present disclosure relates to a method for designing an implant for finger bones, the method including a finger bone image collection step of collecting 3D images of several human finger bones, a finger bone measurement step of measuring the length, cross-sectional width, and thickness of each of the finger bones from the 3D images of the finger bones, and an implant shape derivation step of calculating average values of the lengths, cross-sectional widths, and thicknesses of the finger bones and deriving and storing the shapes of implants for finger bones into a database on the basis of the calculated average values of the cross-sectional widths and thicknesses and shapes of cut surfaces.

BACKGROUND ART

In generally, the bones of a human hand have complicated structures and, as shown in FIG. 1, a thumb, an index finger, a middle finger, a ring finger, and a pinky finger each have a proximal phalange (P) forming the end portion thereof and a metacarpal (M) forming the base thereof.

When a bone of a hand is injured such as cutting or breaking, a surgery of artificially making an artificial hand by inserting an implant (artificial prosthesis) having a shape similar to the proximal phalange and the metacarpal of the finger into the finger bone is performed, and technologies of such implants for finger bones have been disclosed in Korean Patent Application Publication Nos. 1994-7001237 and 2011-0139229.

FIG. 2 is a view showing a surgery that uses such an implant, in which when a lost point of a finger bone is a proximal phalange and a metacarpal, an implant 1 is inserted in each of the proximal phalange P and the metacarpal M, and the inserted implants 1 are connected through a connector 2 and are rotated on the connector 2, thereby performing the function of the lost finger joint.

Meanwhile, when a lost point of a finger bone is any one of a proximal phalange and a metacarpal, a surgery is performed in the way of inserting implants in the upper portion and the lower portion of the lost point of the proximal phalange or the metacarpal and connecting the implant to each other through a connector.

However, since the finger bones of people have different shapes, it is required to design the shapes of implants to be maximally matched to such various shapes.

DISCLOSURE

Technical Problem

The present disclosure has been made in an effort to solve the problems in the related art described above and an objective of the present disclosure is to provide a configuration of a designing method that can easily design shapes of implants, which are used for finger bone surgeries, to corresponding to various shapes.

Technical Solution

The configuration of a method for designing an implant for finger bones of the present disclosure for achieving the objectives includes: a finger bone image collection step of collecting 3D images of several human finger bones, a finger bone measurement step of measuring the length, cross-sectional width, and thickness of each of the finger bones from the 3D images of the finger bones; and an implant shape derivation step of calculating average values of the lengths, cross-sectional widths, and thicknesses of the finger bones and deriving and storing the shapes of implants for finger bones into a database on the basis of the calculated average values of the cross-sectional widths and thicknesses and shapes of cut surfaces.

Advantageous Effects

It was very difficult to fit an implant to a phalange or a metacarpal of a finger bone in the related art, but according to the method for designing an implant for finger bones of the present disclosure, it is possible to easily implement an implant suitable for the shape of a finger bone of a patient, so an effect that it is possible to provide an implant optimized in a patient finger bone-fit type is achieved.

DESCRIPTION OF DRAWINGS

FIGS. 8A and 8B are views showing the shape of a cut surface of a standardization model of a finger bone according to the designing method of an embodiment of the present disclosure, in which FIG. 8A is a view showing the shape of a cut surface of an index finger proximal phalange and FIG. 8B is a view showing variables for determining a cross-sectional shape of the index finger proximal phalange.

FIGS. 9A and 9B are views showing the shape of a cut surface of a standardization model of a finger bone according to the designing method of an embodiment of the present disclosure, in which FIG. 9A is a view showing the shape of a cut surface of a thumb metacarpal and FIG. 9B is a view showing variables for determining a cross-sectional shape of the thumb metacarpal.

BEST MODE

Hereinafter, the configuration of a method for designing an implant for a finger bone according to the present disclosure will be described with reference to the accompanying drawings.

However, the disclosed drawings are provided as examples so that the spirit of the present disclosure can be sufficiently transmitted to those skilled in the art. Accordingly, the present disclosure is not limited to the proposed drawings and may be implemented by other ways.

Further, unless stated otherwise, the terms used herein have meanings that those skilled in the art generally understand, and well-known functions and configurations that may make the main idea of the present disclosure unclear in the following description and the drawings are not described in detail.

Figure 1:
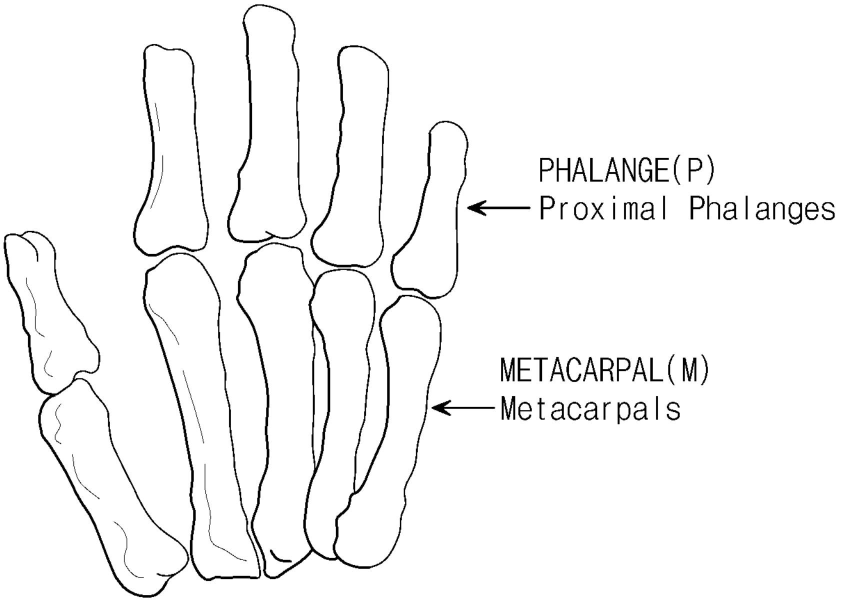
FIG. 1 is a configuration view of the bones of a common human hand.
Figure 2:
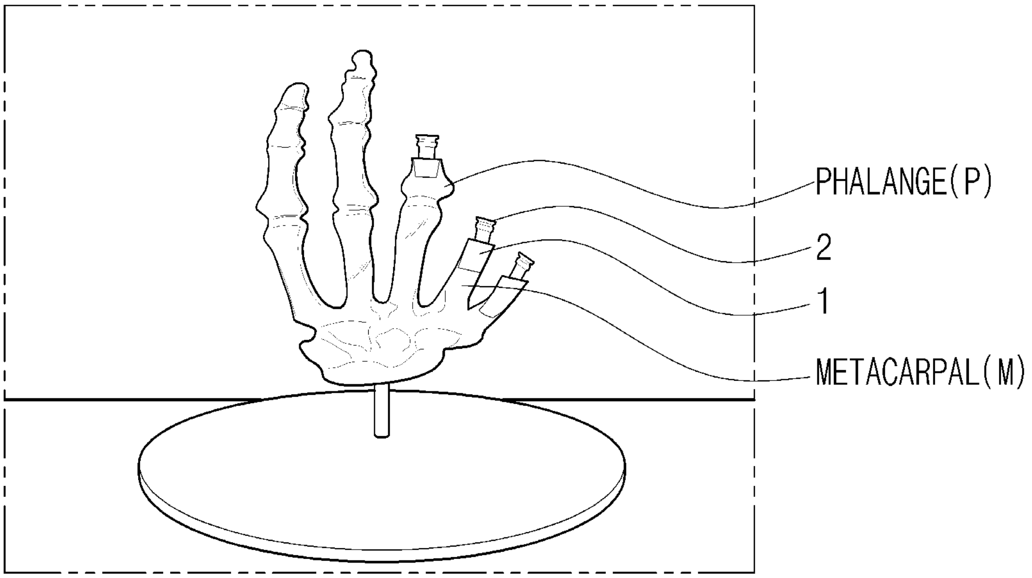
FIG. 2 is a view showing a common implant surgery.
Figure 3:
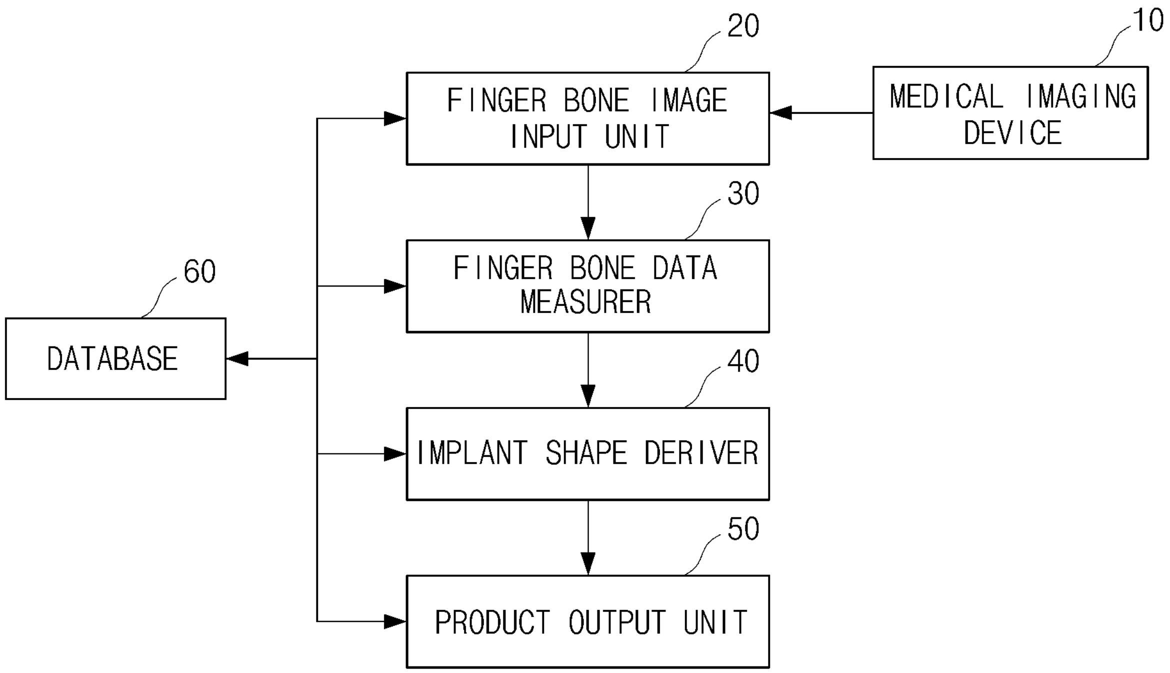
FIG. 3 is a block diagram of a system for implementing a designing method of an embodiment of the present disclosure.

FIG. 3 is a block diagram of a system for implementing a designing method of an embodiment of the present disclosure.

A method for designing an implant for a finger bone of an embodiment of the present disclosure (hereafter, briefly referred to as a 'designing method') is for easily forming the shape of an implant that is inserted into a finger bone, thereby providing an implant optimized in a patient finger bone-fit type.

To this end, the designing method of the present disclosure is implemented in the system shown in FIG. 3.

Referring to the figure, in order to implement of the designing method of the present disclosure, the system includes: a finger bone image input unit 20 that receives 3D images of the finger bones of several people taken by a medical imaging device 10 and stores the 3D images in an interlocked database 60; a finger bone data measurer 30 that measures the length L, the width W, and the thickness T of each of finger bones from the input 3D images of the finger bones; an implant shape deriver 40 that calculates average values of the measured lengths L, widths W, and thicknesses T of the finger bones, and derives and stores the shapes of implants for the finger bones in the database 60 on the basis of the calculated average values of the measured lengths L, widths W, and thicknesses T of the finger bones, and the shapes of cut surfaces; and a product output unit 50 that manufactures implants in accordance with the derived shapes of implants.

As the medical imaging device 10, well-known imaging devices such as a Magnetic Resonance Imaging (MRI) device, a Computed Tomography (CT) device, and an X-ray device may be used, and a CT device is used in an embodiment of the present disclosure.

It is preferable that the finger bone image input unit 20, the finger bone data measurer 30, and the implant shape deriver 40 are implemented by a common computer (not shown) having a monitor, and in detail, it is preferable that the components 20, 30, and 40 are implemented by installing and executing programs in a computer.

Further, it is preferable that a common 3D (3 Dimensions) printer is used as the product output unit 50.

Further, it is preferable to use a storage medium such as a common hard disk or a solid state driver (SSD) installed in a computer as the database 60.

Hereafter, a method for designing an implant for a finger bone of the present disclosure that is implemented by the system of the present disclosure described above is described.

Figure 4:
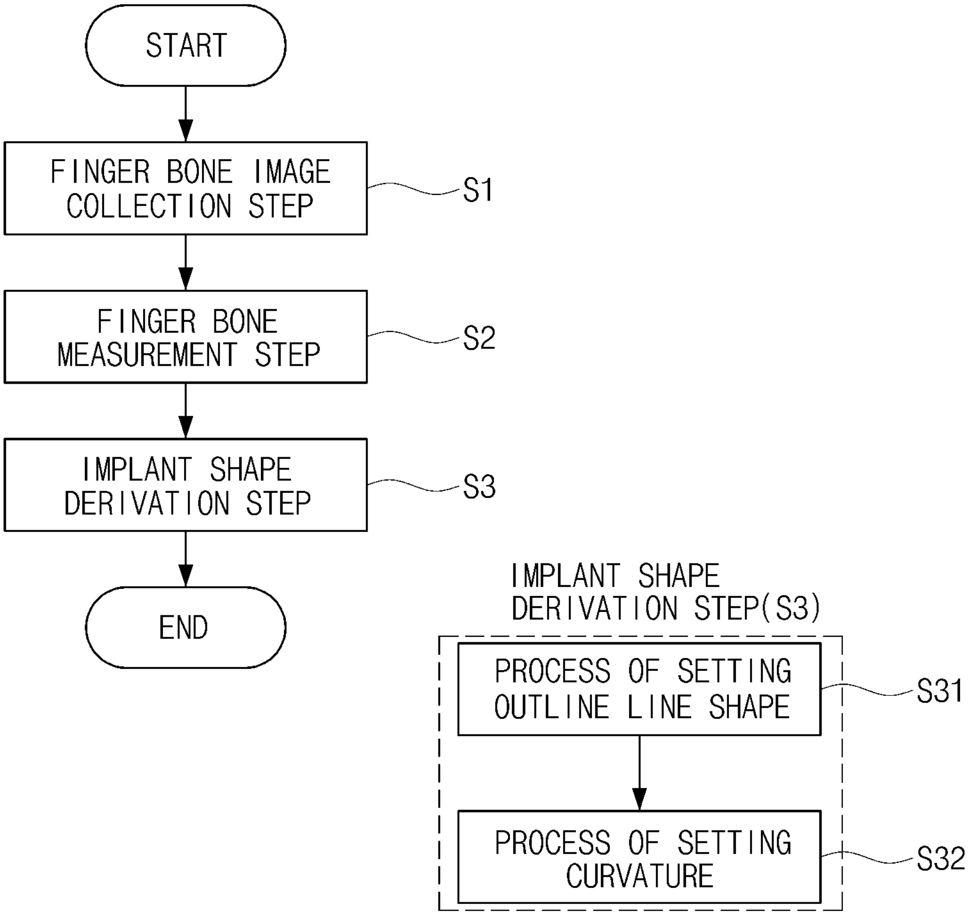
FIG. 4 is a flowchart of a designing method of an embodiment of the present disclosure.

FIG. 4 is a flowchart of the designing method of an embodiment of the present disclosure and the designing method of the present disclosure is described in an article type with reference to the figure.

Finger Bone Image Collection Step (S1)

This is a step of collecting 3D images of finger bones of several people by inputting 3D images of finger bones created by imaging finger bones of at least two or more people through the medical imaging device 10 into the finger bone image input unit 20, and by storing the 3D images in the interlocked database 60.

In an embodiment of the present disclosure, one man and one woman who are the shortest (a total of two people) and one man and one woman who are the tallest (a total of two people) were selected from 57 adult men and 55 adult women, three men and three women (a total of six people) who have heights in a range between the largest height and the smallest height were freely selected, whereby 3D images of finger bones were created by imaging the finger bones of a total of 10 men and women through a CT device that is the medical imaging device, and the created 3D images were stored in the interlocked database 60.

The following Table 1 shows the sex and height of collected data and remarks.

TABLE 1

| No. | Sample Number | Sex | Height(cm) | Remarks |
|---|---|---|---|---|
| 1 | f_008 | Female | 146 | Smallest height (woman) |
| 2 | m_024 | Male | 146 | Smallest height (man) |
| 3 | f_014 | Female | 150 | |
| 4 | m_023 | Male | 150 | |
| 5 | f_001 | Female | 156 | |
| 6 | f_021 | Female | 160 | |
| 7 | m_022 | Male | 165 | |
| 8 | f_049 | Female | 165 | Largest height (woman) |
| 9 | m_025 | Male | 170 | |
| 10 | m_006 | Male | 178 | Largest height (man) |

2) Finger Bone Measurement Step (S2)

This is a step in which the finger bone data measurer 30 measures the length L, cross-sectional width W, and thickness T of each finger bone from the 3D images of finger bones input and stored in the database 60.

In an embodiment of the present disclosure, the lengths L of osseointegration implants of the proximal phalange of the index finger, the metacarpal of the index finger, and the metacarpal of the thumb of the finger bones of each of the selected 10 adult men and women (5 men and 5 women) described in Table 1 were measured.

Figure 5:
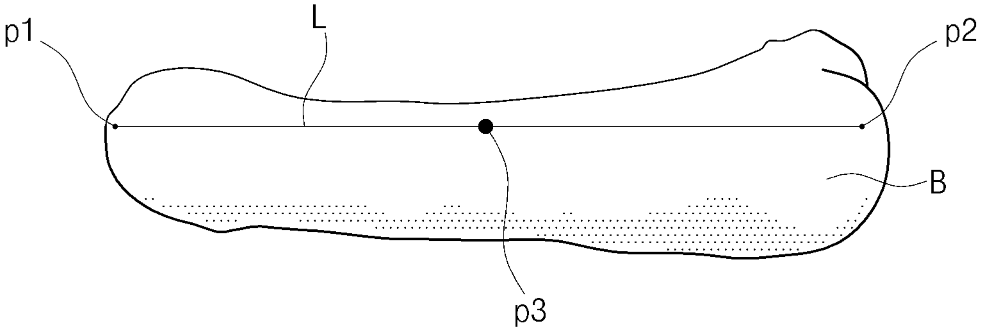
FIG. 5 is a view showing measurement of the length of a finger bone in the designing method of an embodiment of the present disclosure.

FIG. 5 is a view showing measurement of the length of a finger bone in the designing method of an embodiment of the present disclosure, in which in order to measure the entire length of a finger bone B, the length from a head point p1 at the upper portion and a bottom point p2 at the lower portion of the bone B that are visually observed from a 3D image of the finger bone is measured, and the measured length is determined as the entire length L of the finger bone.

Figure 6:
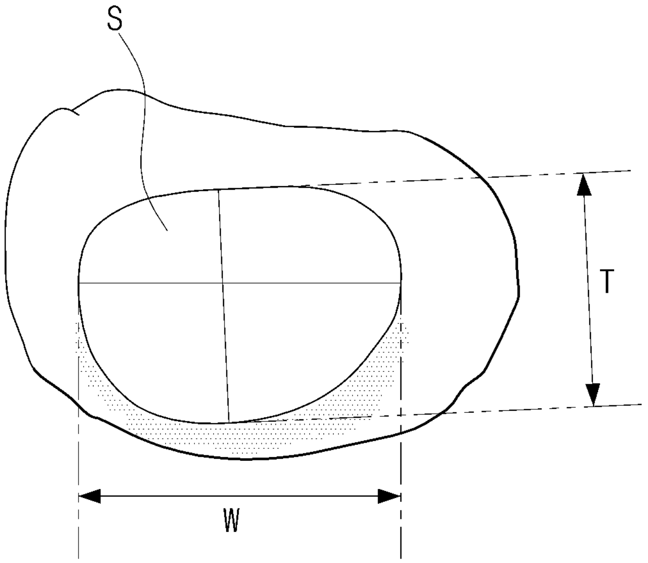
FIG. 6 is a view showing measurement of the width and the thickness of a finger bone in the designing method of an embodiment of the present disclosure.

FIG. 6 is a view showing measurement of the width and the thickness of a finger bone in the designing method of an embodiment of the present disclosure, in which a cross-sectional width W in a Medio-Lateral direction of a cut surface 's' and a thickness T in an Antero-Posterior direction of the cut surface 's' at a point (point p3 in FIG. 5) of the finger bone that corresponds to an intermediate value (½ point of the entire length) of the entire length L measured on a 3D image of the finger bone were measured.

The following Table 2 is a table showing the entire length L, a cross-sectional width W, and a thickness T of each finger bone measured on the 3D images of the finger bones of the selected people in Table 1 in an embodiment of the present disclosure.

TABLE 2

| Ssample | Distal Phalange(Index) | | | Metacarpal(Index) | | | Thumb Metacarpal | | | |
|---|---|---|---|---|---|---|---|---|---|---|
| Number | L | W | T | L | W | T | L | W | T | Remarks |
| f_008 | 35.18 | 8.76 | 7.32 | 57.76 | 9.58 | 7.46 | 38.63 | 11.39 | 8.52 | |
| m_024 | 39.56 | 10.21 | 8.16 | 60.1 | 9.78 | 9.08 | 42.8 | 12.77 | 10.35 | |
| f_014 | 36.33 | 6.49 | 7.94 | 56.5 | 8.49 | 7.96 | 39.34 | 10.25 | 8.29 | |
| m_023 | 40.96 | 9.34 | 7.15 | 60.77 | 9.14 | 7.97 | 41.88 | 11.79 | 8.05 | |
| f_001 | 36.97 | 8.14 | 5.92 | 60.96 | 8.58 | 7.7 | 47.28 | 9.8 | 8.01 | |
| f_021 | 37.49 | 9.36 | 7.35 | 59.36 | 9.3 | 8.35 | 42.67 | 11.86 | 9.09 | |
| m_022 | 34.36 | 10.42 | 7.39 | 55.94 | 9.32 | 9.43 | 45.75 | 12.65 | 8.72 | |
| f_049 | 37.17 | 9.64 | 7.48 | 61.32 | 10.28 | 9.14 | 41.84 | 13.46 | 9.95 | |
| m_025 | 40.27 | 8.66 | 7.09 | 60.16 | 8.32 | 8.81 | 46.24 | 10.67 | 7.89 | |
| m_006 | 48.61 | 10.18 | 12.89 | 59.79 | 11.77 | 10.44 | 47.5 | 13.78 | 10.9 | |

3) Implant Shape Derivation Step (S3)

This is a step in which the implant shape deriver 40 calculates average values of the measured lengths L, cross-sectional widths W, and thicknesses T of the finger bones, and derives and stores shapes of implants for the finger bones in the database 60 on the basis of the calculated average values of the lengths L, cross-sectional widths W, and thicknesses T, and the shapes of cut surfaces.

In an embodiment of the present disclosure, a length average, a width average, and a thickness average of corresponding finger bones were calculated by adding up all data of the lengths L, cross-sectional widths, and thicknesses T obtained through Table 2 for each kind, and then dividing the data by the number of the people.

The following shows the calculated largest length Max Length, smallest length Min Length, and average of lengths Length average of each finger bone, and the largest cross-sectional width Max Width, the smallest cross-sectional width Min Width, and the average of the cross-sectional widths Width average of the fingers, and the largest thickness Max Thickness, the smallest thickness Min Thickness, and the average of the thicknesses Thickness average.

| Distal Phalange(Index) | Metacarpal(Index) | Thumb Metacarpal |
|---|---|---|
| Length average: 38.69<br>Width average: 9.12<br>Thickness average: 7.87 | Length average: 59.27<br>Width average: 9.46<br>Thickness average: 8.63 | Length average: 49.39<br>Width average: 11.84<br>Thickness average: 8.98 |
| Max Length: 48.61<br>Max Width: 10.42<br>Max Thickness: 12.89<br>Min Length: 34.36<br>Min Width: 6.49<br>Min Thickness: 5.92 | Max Length: 61.32<br>Max Width: 11.77<br>Max Thickness: 10.44<br>Min Length: 55.94<br>Min Width: 8.32<br>Min Thickness: 7.46 | Max Length: 47.5<br>Max Width: 13.78<br>Max Thickness: 10.9<br>Min Length: 38.63<br>Min Width: 9.8<br>Min Thickness: 7.89 |

Figure 7A:
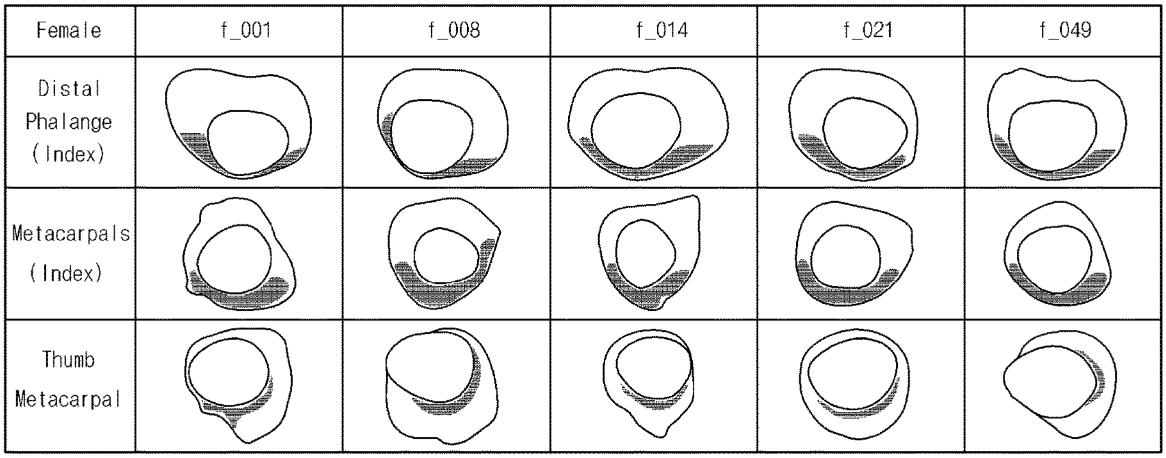
FIGS. 7A and 7B are views showing shapes of cut surfaces of finger bone models according to the designing method of an embodiment of the present disclosure.
Figure 7B:
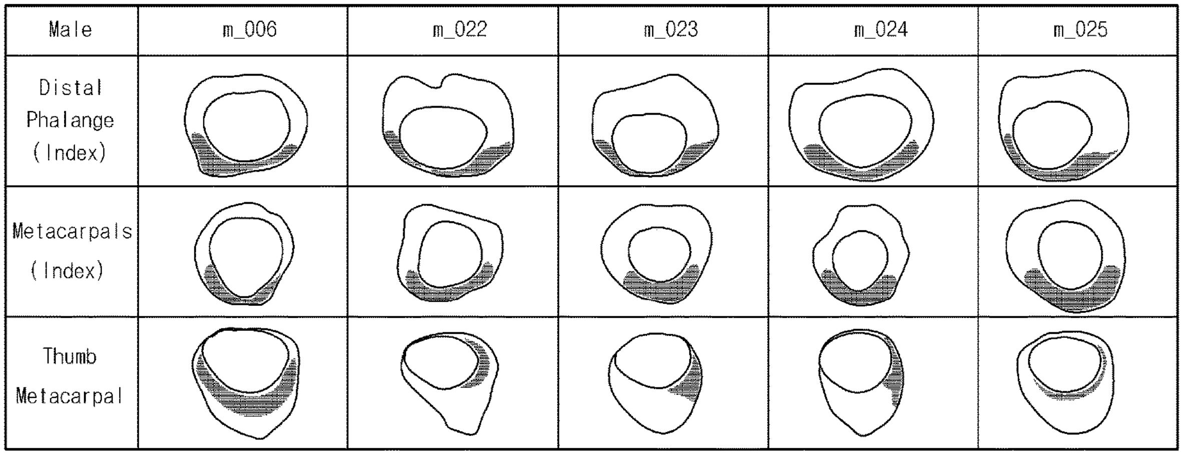

FIGS. 7A and 7B are views showing shapes of cut surfaces of finger bone models according to the designing method of an embodiment of the present disclosure, which show images of cut surfaces 's' at a point (point p3 in FIG. 5) of finger bones that corresponds to an intermediate value (½ point of the entire length) of the entire lengths measured on 3D images of the finger bones.

Next, as described above, the average value of the entire lengths L, the average value of the cross-sectional widths W, and the average value of the thicknesses T are obtained, and then the implant shape deriver 40 derives shapes of implants for the finger bones on the basis of the average values and the shapes of the cut surfaces of the finger bones.

In this case, the implant shape deriver 40 derives shapes of implants on the basis of the average values and the shapes of the cut surfaces, and this derivation process is composed to the following two processes.

3-1) Process of Setting Outline Line Shape of Cut Surface of Implant (S31)

This is a process of setting an outline line shape of a cut surface of a finger bone, in which the implant shape deriver 40 creates a standardization model having the average values of the measured lengths L, cross-sectional widths W of the cut surfaces, and thicknesses T of the finger bones.

Figure 8A:
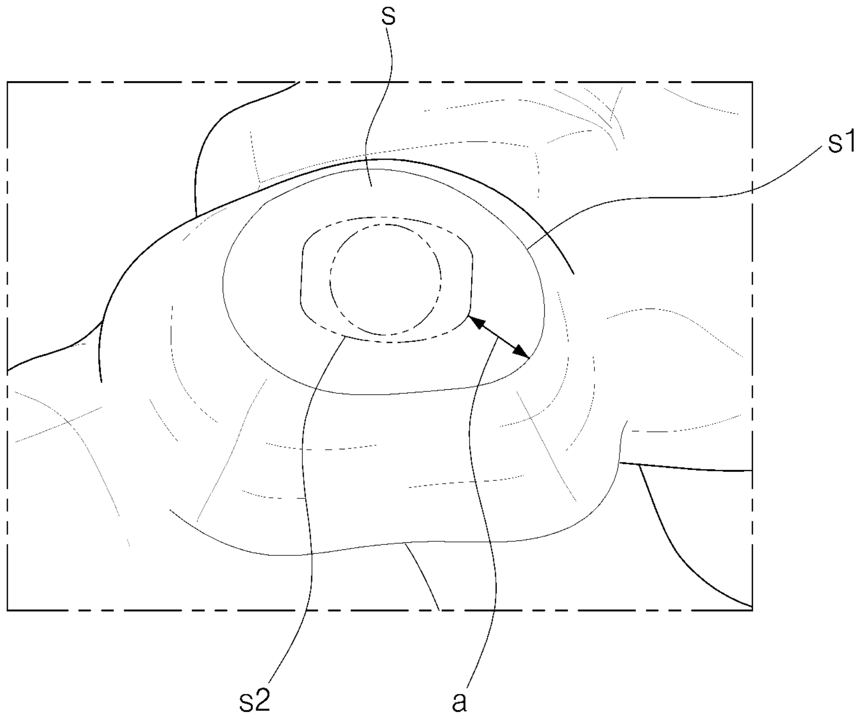
Figure 8B:
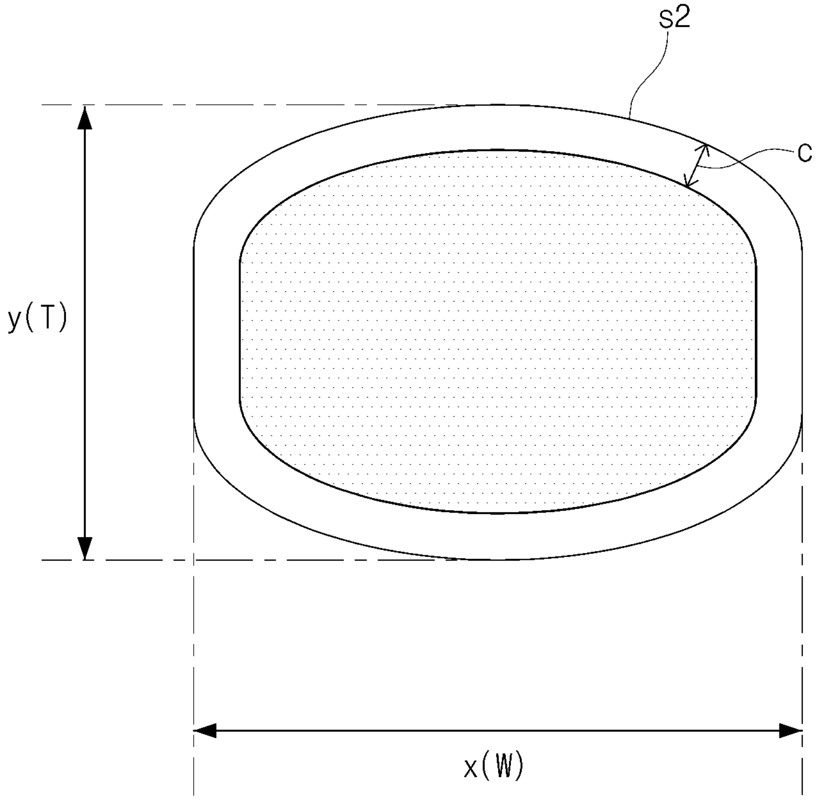

FIGS. 8A and 8B are views showing the shape of a cut surface of a standardization model of a finger bone according to the designing method of an embodiment of the present disclosure, in which FIG. 8A is a view showing the shape of a cut surface of an index finger proximal phalange and FIG. 8B is a view showing variables for determining a cross-sectional shape of the index finger proximal phalange.

Referring to FIGS. 8A and 8B, the implant shape deriver 40, in order to derive an outline shape of the cut surface of the created standardization model, calculates a closed curve s2 spaced a predetermined distance 'a' inward along the outermost line s1 of the distal direction of the cut surface 's' of the standardization model, and sets the calculated shape of the closed curve s2 as an outline shape of a cut surface of an implant.

Figure 9A:
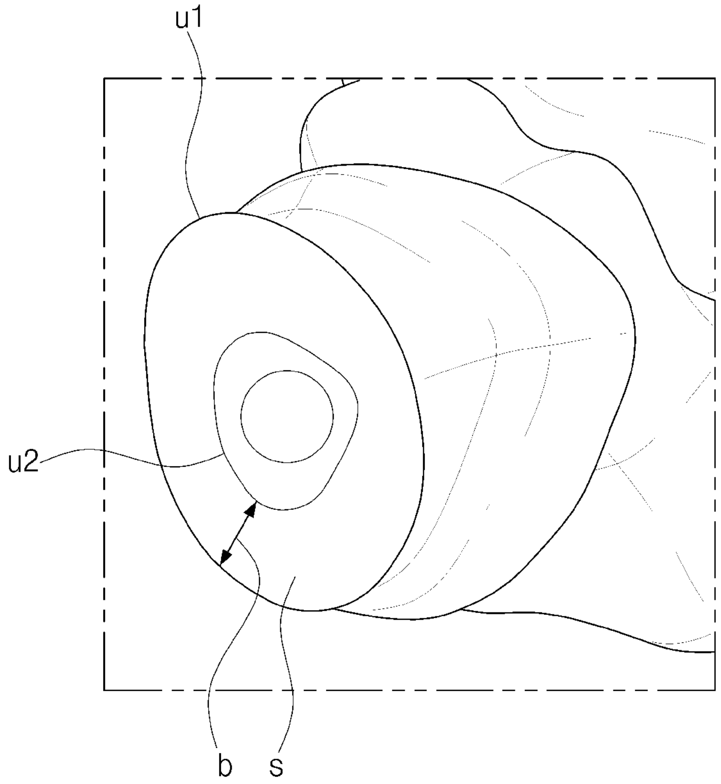
Figure 9B:
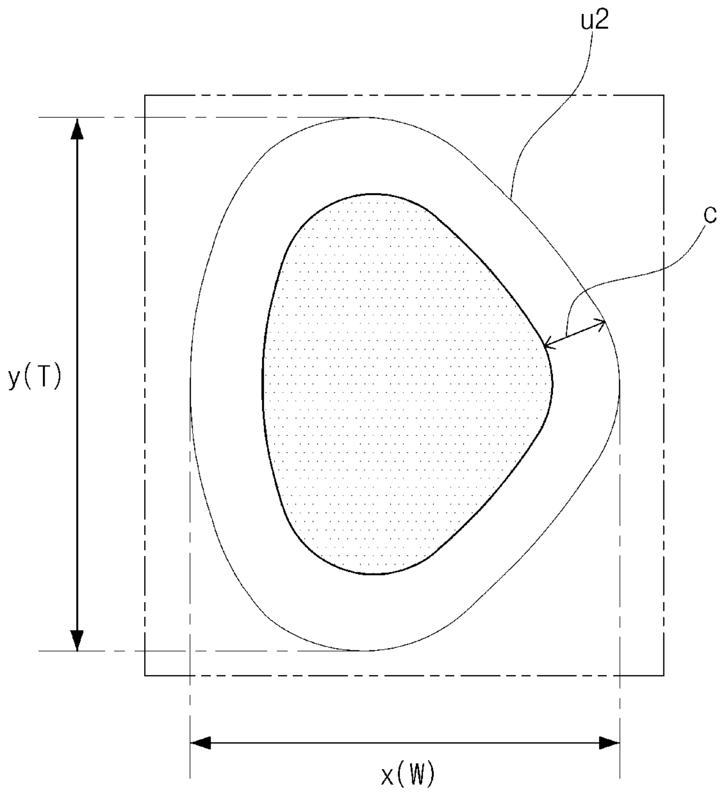

FIGS. 9A and 9B are views showing the shape of a cut surface of a standardization model of a finger bone according to the designing method of an embodiment of the present disclosure, in which FIG. 9A is a view showing the shape of a cut surface of a thumb metacarpal and FIG. 9B is a view showing variables for determining a cross-sectional shape of the thumb metacarpal.

Referring to FIGS. 9A and 9B, the implant shape deriver 40, in order to derive an outline shape of the cut surface of the created standardization model, calculates a closed curve u2 spaced a predetermined distance 'b' inward along the outermost line u1 of the distal direction of the cut surface 'u' of the standardization model, and sets the calculated shape of the closed curve u2 as an outline shape of a cut surface of an implant.

Further, when the outline shape of the implant is set as described above, in order to manufacture the shape of the implant into a patient-fit type, the values of the cross-sectional width W and the thickness T of the cut surface are made into variables x and y such that the values of the cross-sectional width W and the thickness can be adjusted while a constant outline shape is provided.

Figure 10:
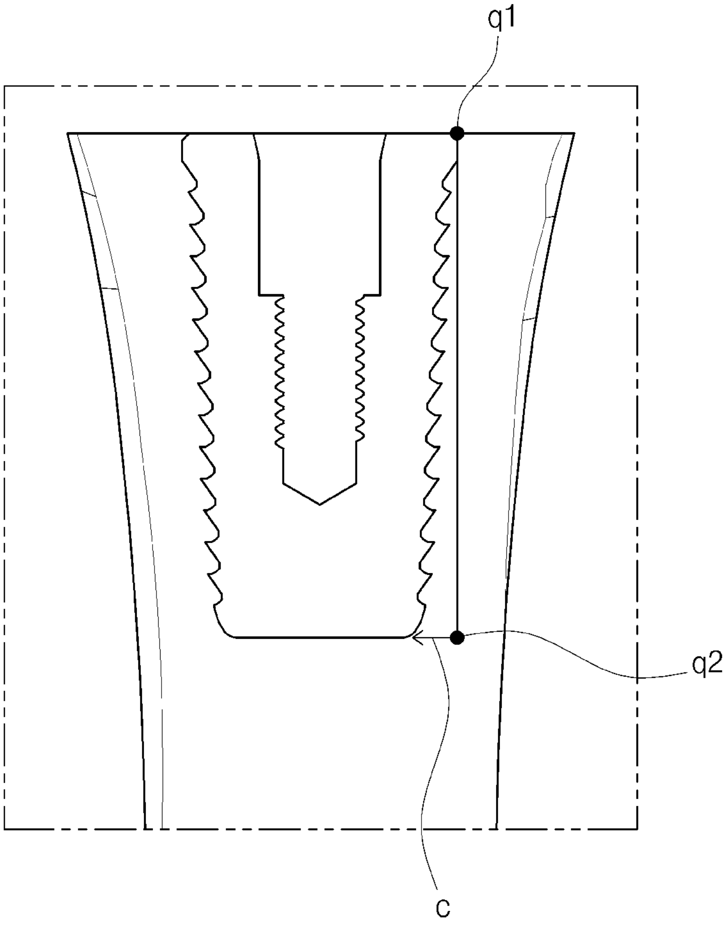
FIG. 10 is a view showing diameter variation of a body from a head point q1 to a bottom point p2 of a finger bone.

FIG. 10 is a view showing diameter variation of a body from a head point q1 to a bottom point p2 of a finger bone, in which the implant shape deriver 40, in order to apply a shape according to diameter variation from the head point q1 to the bottom point q2 of a finger bone, sets the diameter of the bottom point q2 shorter inwardly by an offset distance 'c' than the diameter of the head point q1. Further, in an embodiment of the present disclosure, an offset distance 'c' was set as 0.45 mm for the phalange of an index finger was sea, as shown in FIG. 8B, and the offset distance 'c' was set as 1 mm for the metacarpal of a thumb, as shown in FIG. 9B.

The offset distance 'c' is used as a constant when a curvature according to the entire length L of an implant to be described above is calculated, and is for keeping a remaining thickness for forming threads (M2.5 threads) of an implant.

3-2) Process of Setting Curvature in Sagittal Direction of Implant (S32)

This is a process in which the implant shape deriver 40 sets a curvature in a sagittal direction of a standardization model of a finger bone.

Figure 11:
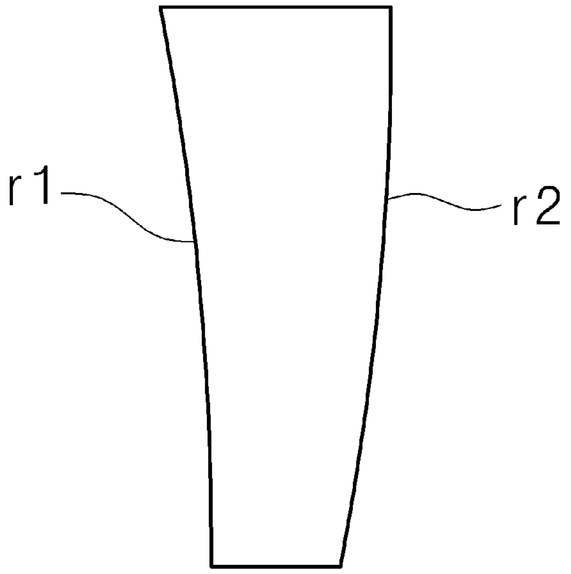
FIG. 11 is a schematic view for determining the curvature of an implant according to the designing method of an embodiment of the present disclosure.
Figure 12:
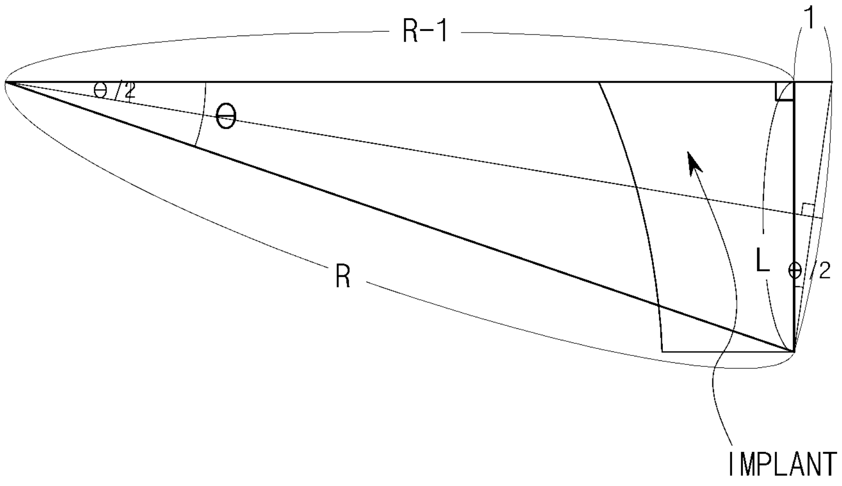
FIG. 12 is a partial enlarged view of the schematic view shown in FIG. 11.

FIG. 11 is a schematic view for determining the curvature of an implant according to the designing method of an embodiment of the present disclosure and FIG. 12 is a partial enlarged view of the schematic view shown in FIG. 11.

Referring to FIG. 11, in order to prevent an empty space in a medullary cavity when an implant is perpendicularly inserted, the implant shape deriver 40 positions the center of a curved surface r1 of an axial anterior of a standardization model of a finger bone at a lower portion of an implant and the center of a curved surface r2 of a posterior at an upper portion of the implant.

In this case, as shown in FIG. 12, when the length from the center of the curved surface r2 of the posterior to the lowermost end of the entire length L of the finger bone is R, it is possible to set the curvature of the curved surface r1 of the anterior and the curvature of the curved surface r2 of the posterior in the axial direction of the implant in accordance with the entire length of an implant to be inserted into a medullary cavity, and this calculation process is described with reference to FIG. 12.

The diameters of the top t1 and the bottom t2 of the body of an implant are different by the offset distance 'c' described above, and the following Equation 1 can be derived under the assumption that the entire length L of the body t can be infinitely increased.

$$\tan \theta/2 = L/(2(R-c)) = 1/L \qquad \text{(Equation 1)}$$

c: offset distance (mm)

The following Equation 2 can be obtained by arranging Equation 1 as a relational expression about R.

$$R = L^2/2 + c \qquad \text{(Equation 2)}$$

c: offset distance (mm)

Accordingly, when R shown in FIG. 12 is obtained by the method described above, it is possible to set the curvature of the curved surface r1 of the anterior and the curvature of the curved surface r2 of the posterior in the axial direction of the implant.

Accordingly, it is possible to create a standardization model of an implant through the process of setting an outline shape of a cut surface of an implant (S31) and the process of setting a curvature in a sagittal direction of an implant (S32).

DESCRIPTION OF THE REFERENCE NUMERALS

10: medical imaging device
20: finger bone image input unit
30: finger bone data measurer

40: implant shape deriver
50: product output unit
60 database

The invention claimed is:

1. A method for designing an implant for a finger bone of a patient, implemented by a system including a medical imaging device, a finger bone image input unit, a finger bone data measurer, and an implant shape deriver, the method comprising:

a finger bone image collection step, including creating 3D images by imaging finger bones of at least two people through the medical imaging device, and storing the 3D images in a database through the finger bone image input unit;

a finger bone measurement step of measuring, by the finger bone data measurer, a length, a cross-sectional width, and a thickness of each finger bone based on the 3D images stored in the database; and an implant shape derivation step, performed by the implant shape deriver, and including: calculating average values of the measured length, cross-sectional width, and thickness of each finger bone; deriving a shape of the implant for the patient on the basis of the calculated average values of the length, cross-sectional width, and thickness, and a shape of a cut surface of each finger bone on the 3D images, and storing the derived shape of the implant in the database, wherein the implant shape derivation step further includes:

an outline shape setting step of generating, by the implant shape deriver, a standardization model for the implant based on the average values of the measured length, cross-sectional width, and the thickness of each finger bone, such that an outline shape of a cut surface of the standardization model is set; and a curvature setting step of setting, by the implant shape deriver, a curvature in a sagittal direction of the standardization model, and wherein, in the curvature setting step, the implant shape deriver, to prevent an empty space in a medullary cavity when the implant is perpendicularly inserted, sets a curvature of an anterior curved surface and a curvature of a posterior curved surface in an axial direction of the implant in accordance with a length of the implant to be inserted into the medullary cavity.

2. The method of claim 1, wherein, in the finger bone measurement step, measuring the length of each finger bone includes measuring a length from a head point at an upper portion to a bottom point at a lower portion of each finger bone based on the 3D images measuring the cross-sectional width and the thickness of each finger bone respectively includes measuring a cross-sectional width in a mediolateral direction and a thickness in an anteroposterior direction of a cut surface at a point of each finger bone, wherein the point is a midpoint between the head point and the bottom point of each finger bone on the 3D images.

3. The method of claim 1, wherein the outline shape setting step includes calculating a shape of a closed curve spaced a predetermined distance inward along an outermost line of a distal direction of the cut surface of the standardization model, and setting the calculated shape of the closed curve as an outline shape of a cut surface of the implant.

4. The method of claim 3, wherein the outline shape setting step further includes adjusting a cross-sectional width and a thickness of the cut surface of the implant by parameterizing values thereof, while maintaining the outline shape of the implant constant.

5. The method of claim 3, wherein, in the outline shape setting step, the implant shape deriver, in order to reflect a diameter variation from a head point to a bottom point of each finger bone, sets a diameter of a bottom point of the implant shorter inwardly by an offset distance than a diameter of the head point of the implant.

6. The method of claim 1, wherein, in the curvature setting step, when diameters of a top and a bottom of a body of the implant are different by an offset distance, and a length from the center of a posterior curved surface to a lowermost end of the implant is R, R is determined according to Equation 1 and Equation 2, wherein Equation 1 is $$\tan \theta/2 = L/(2(R-c)) = 1/L,$$

wherein c denotes the offset distance and L denotes a length from a head point at an upper portion to a bottom point at a lower portion of the implant, and wherein Equation 2 is $$R = L^2/2 + c,$$

wherein c denotes the offset distance and L denotes the length from the head point to the bottom point of the implant.

* * * * *